United States Patent
Schmitz-Rode et al.

(10) Patent No.: US 6,533,716 B1
(45) Date of Patent: Mar. 18, 2003

(54) SELF-DEPLOYING AXIAL-FLOW PUMP INTRODUCED INTRAVASCULARLY FOR TEMPORARY CARDIAC SUPPORT

(76) Inventors: Thomas Schmitz-Rode, Kupferstrasse 5, 52070 Aachen (DE); Rolf W. Günther, Brüsseler Ring 73c, 52074 Aachen (DE)

( * ) Notice: Subject to any disclaimer, the term of this patent is extended or adjusted under 35 U.S.C. 154(b) by 0 days.

(21) Appl. No.: 09/623,687
(22) PCT Filed: Jan. 20, 1999
(86) PCT No.: PCT/EP99/00368
 § 371 (c)(1),
 (2), (4) Date: Sep. 7, 2000
(87) PCT Pub. No.: WO99/44651
 PCT Pub. Date: Sep. 10, 1999

(30) Foreign Application Priority Data

Mar. 7, 1998 (DE) .................... 298 04 046 U

(51) Int. Cl.$^7$ ................................. A61N 1/12
(52) U.S. Cl. ....................................... 600/16
(58) Field of Search .................... 600/16, 17; 623/3.13, 623/3.15, 903, 904; 416/176, 177, 203, 228, 235, 237; 418/201.1, 220

(56) References Cited

U.S. PATENT DOCUMENTS

| | | | | |
|---|---|---|---|---|
| 4,753,221 A | * | 6/1988 | Kensey et al. ................. | 128/1 |
| 4,919,647 A | * | 4/1990 | Nash ........................... | 600/16 |
| 4,969,865 A | * | 11/1990 | Hwang et al. ................ | 600/16 |
| 6,168,624 B1 | * | 1/2000 | Sudai ........................ | 623/3.21 |

* cited by examiner

Primary Examiner—George R. Evanisko
Assistant Examiner—Frances P. Oropeza
(74) Attorney, Agent, or Firm—Diller, Ramik & Wight

(57) ABSTRACT

The axial-flow pump for introduction through the vascular system of a patient has a flexible compressible tube (1) forming the pump housing. A radially compressible rotor (7) is located within the tube (1). The drive shaft (6) of the rotor (7) extends through a catheter (4). The catheter (4) can be pulled into a cover hose (5) together with the tube (1) and the rotor (7).

18 Claims, 3 Drawing Sheets

SELF-DEPLOYING AXIAL-FLOW PUMP INTRODUCED INTRAVASCULARLY FOR TEMPORARY CARDIAC SUPPORT

The invention relates to a self-deploying axial-flow pump to be introduced intravascularly for temporary cardiac support.

BACKGROUND OF THE INVENTION

In a cardiogenic shock, the ejection rate of the left ventricle is substantially reduced. The lowered supply to the heart can lead to irreversible heart failure. A temporary support system for the left ventricle is used to take over a part of or the entire pump function of the left ventricle and to improve the coronary perfusion. In cardiac surgery, such a system can be used for the left and the right ventricle and may replace a heart-lung machine.

A system for percutaneous implantation that has gained some clinical importance, is the intra-aortal balloon counterpulsation (IABP). However, the haemodynamic improvement achievable is rather limited.

After experimental and preliminary clinical tests, a known axial-flow pump "Hemopump™" for transfemoral implantation appears to be a promising concept that might achieve a sufficient relief of the left ventricle. The intake stud of the pump is placed retrogradely above the aorta valve in the left ventricle. The pump rotor is located at the end of a cannula in the upper aorta descendens and is driven by an external motor. It is a disadvantage of this system that, due to the large diameter of the motor, the transfemoral implantation is possible only surgically through a femoral arteriotomy and, eventually, a graft coupling.

SUMMARY OF THE INVENTION

It is the object of the present invention to provide a transfemorally insertable axial-flow blood pump for cardiac support that may be introduced intravascularly without an operation.

The radial compressibility of the elements allows to realize a small puncture diameter acceptable for a percutaneous implantation following the Seldinger technique. By deploying the device in the cardiovascular system, a relatively large pump diameter of 10 to 14 mm can be provided. Thereby, the rotor speed, and thus the mechanical stress on the elements, is lowered.

The following is a detailed description of an embodiment of the invention, given with reference to the drawings.

DESCRIPTION OF THE PREFERRED EMBODIMENTS

Figure 1:
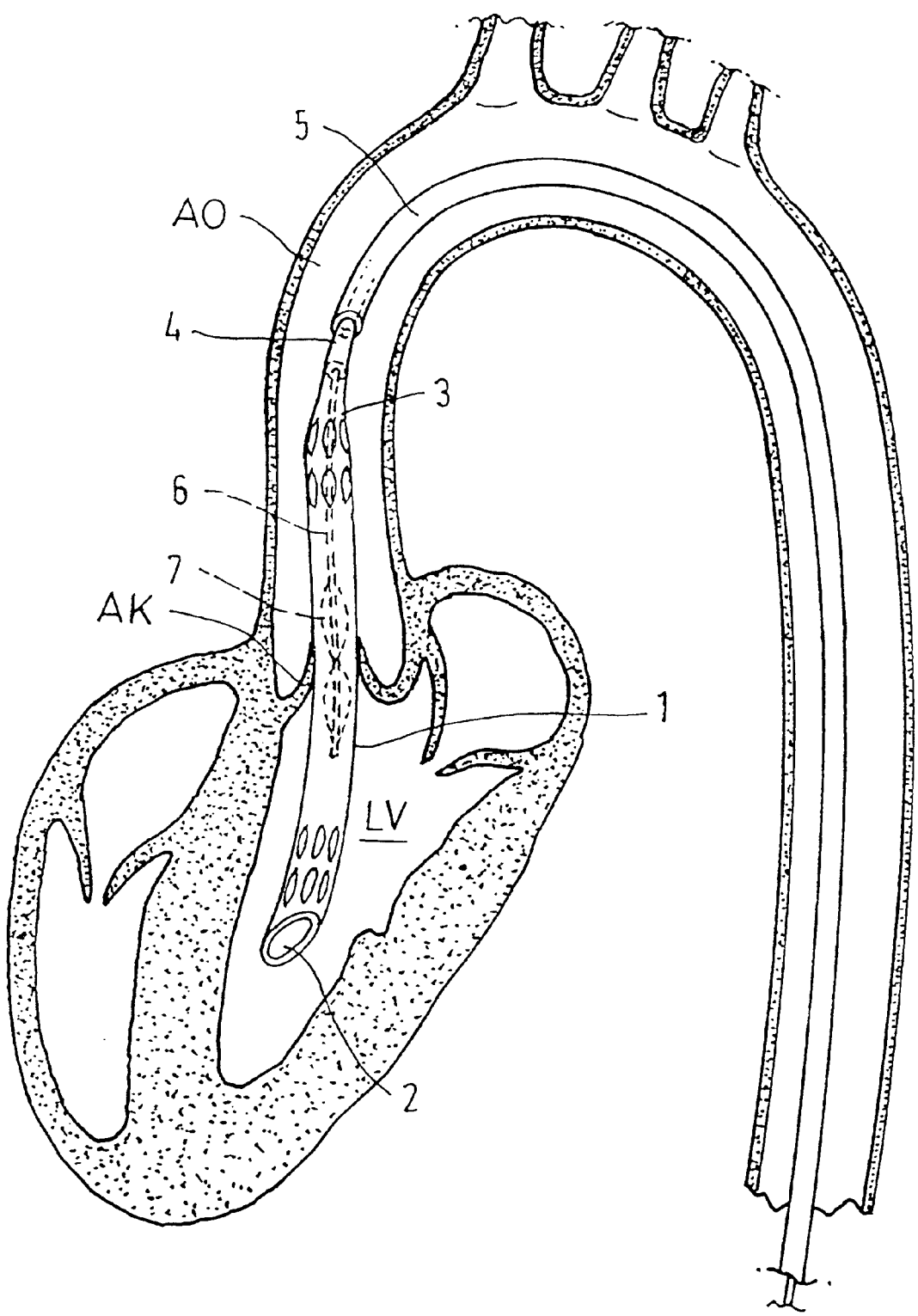
FIG. 1—a parasagittal view of the axial-flow pump after placement above the aortal valve, with the tip in the left ventricle of the heart, FIG. 2a—an enlarged representation of the distal end portion of the tube, FIG. 2b—an enlarged representation of the proximal end portion of the tube, and FIG. 3—an illustration of the deployed rotor.

FIG. 1 illustrates the pump system for support of the left ventricle, in position. The intake tube 1 has a tip 2 in the left ventricle LV. The distal end 3 is located in the aorta ascendens AO and passes into a catheter 4 covered by a cover hose 5. The catheter and the cover hose exit through the puncture in the inguinal artery. The catheter 4 accommodates a flexible rotatable shaft 6 driven from outside by a motor, the tip of the shaft being provided with a self-deploying rotor 7. The rotor 7 is situated within the tube 1. The outer diameter of the deployed rotor 7 is minimally smaller than the inner diameter of the deployed tube 1 so that the rotor 7 fills almost the entire cross section of the tube and is guided rotating in the tube 1. To position the system, the tube 1 and the rotor 7 are radially compressed and covered by the tubular cover hose 5 advanced up to the tube tip 2. In this configuration, the system is advanced percutaneously over a guide wire following the Seldinger technique, the tip being moved through the aortal valve AK into the left ventricle LV. Deploying is effected by withdrawing the cover hose 5 on the fixed catheter 4 until the tip of the cover hose has exposed the tube end 3. To remove the system, the cover hose 5 is advanced to the tube tip 2, whereby the rotor 7 and the tube are pulled into the cover hose 5 in the compressed state, the latter then being extracted through the puncture.

Figure 2A:
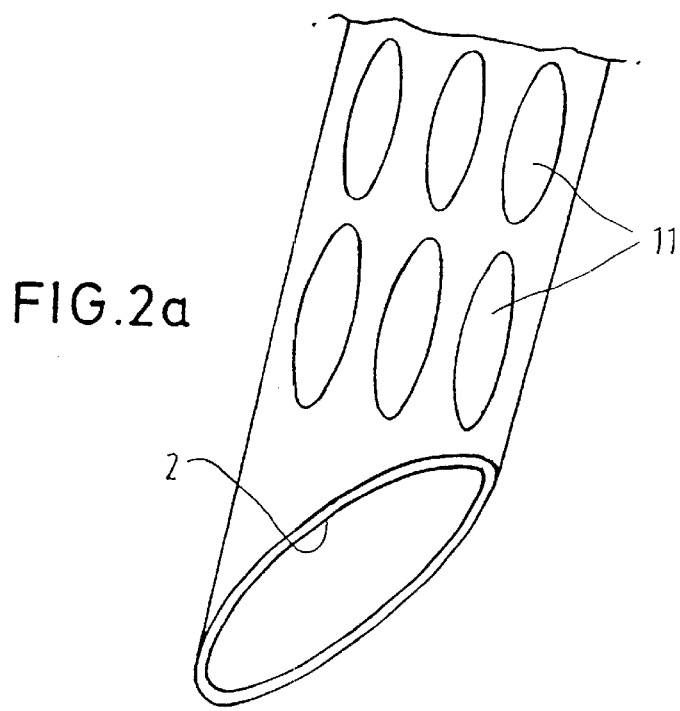
Figure 2B:
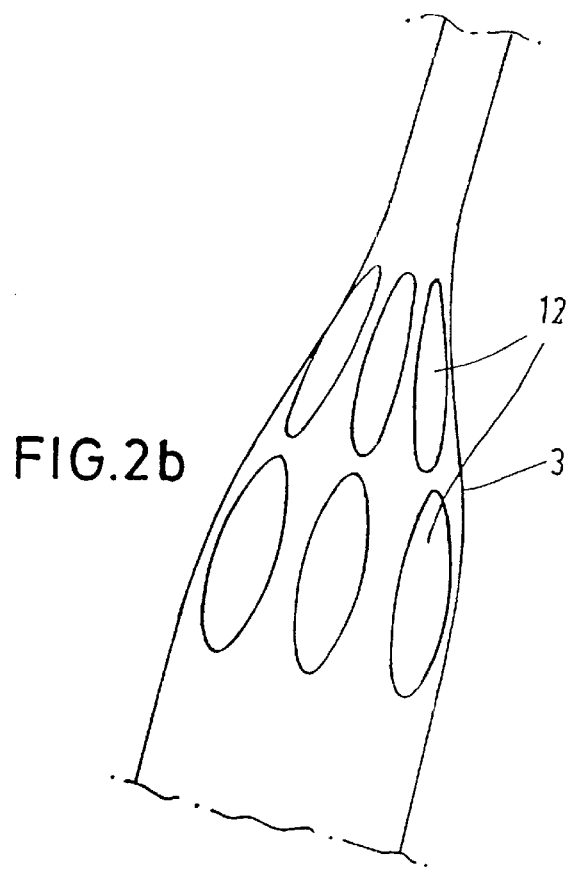

FIG. 2 illustrates design details of the tube 1. The tip may be beveled to increase the intake cross section (FIG. 2a). Further, lateral holes 11 may be provided. The tapering tip 3 of the tube has a plurality of outlet holes 12 that may be circular or slit-shaped (FIG. 2b). Preferably, the tube 1 is made of a plastic coated self-expanding metal endoprosthetic material with a diameter of 10 to 14 mm and a length of 7 to 12 cm after deployment.

Figure 3:
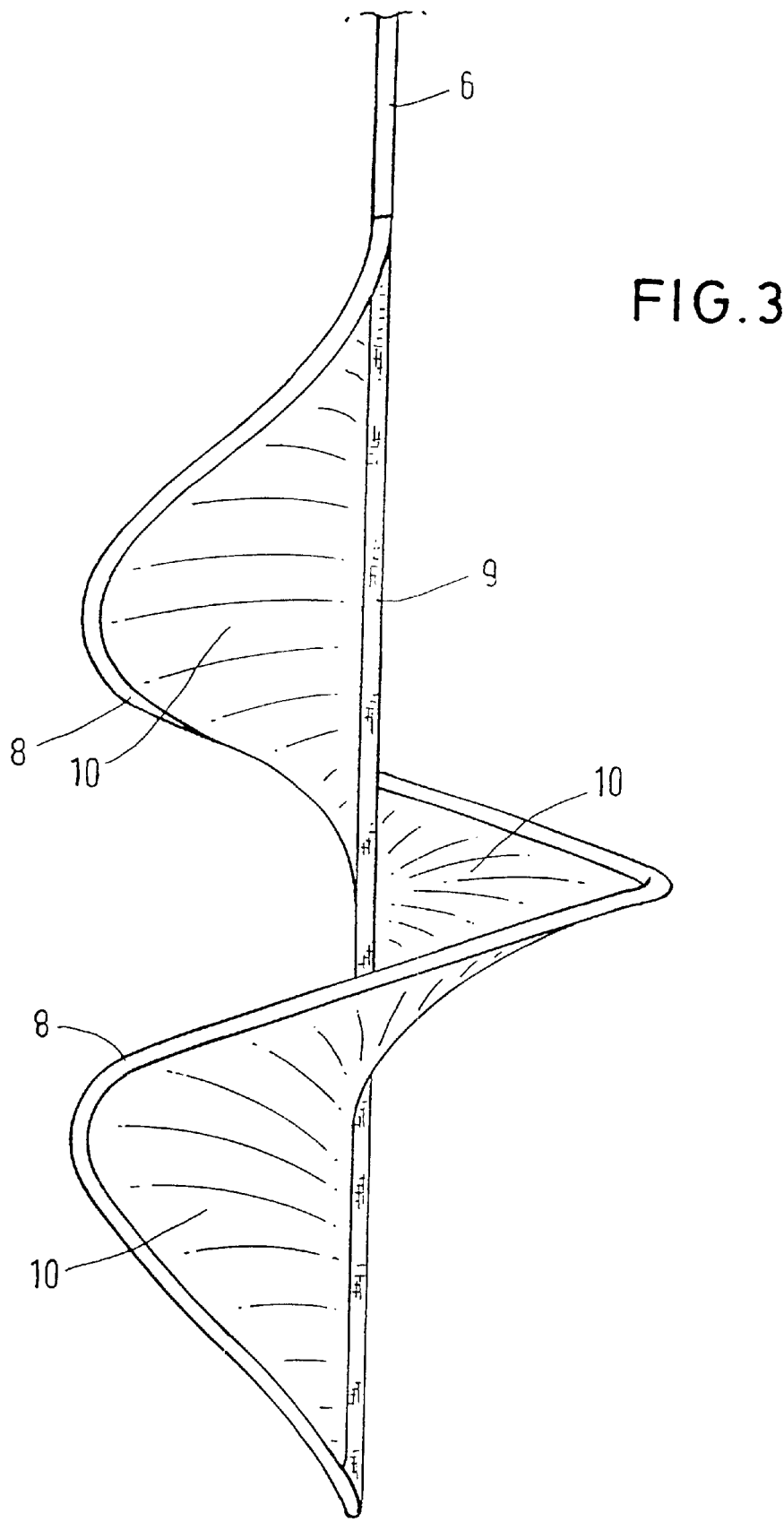

FIG. 3 illustrates an exemplary design of the deployable rotor 7 taking the form of an Archimedean spiral. The latter consists of a helix 8 of memory metal (Nitinol), both ends of which terminate under an acute angle in the central axis and are connected by an elastic band 9. The band 9 extends along the central axis (axis of rotation) of the helix 8. The helical rotor blade is formed by an elastic cover 10 made from spongy cross-woven tissue 10 extending between the helix 8 and the band 9. The preferred material of the cover is a net-shaped highly elastic plastic material matrix coated with a thin silicon or polyurethane skin. The orientation of the cover surface is defined by a certain point on the helix 8 and the respective next point on the band 9 (axis of rotation) are connected by a straight line.

Minimally, the rotor consists of one complete winding (360°) of the helix plus the acute-angled termination of the helix at both ends thereof (FIG. 3). However, it may also consist of 1 ½, 2 or a plurality of full windings of the helix.

In the compressed state, the helix wire 8 extends elongated in the central axis, surrounded by the compressed tube 1 within the cover hose 5. The elastic band 9 is under maximum tension, the elastic cover tissue 10 is compressed. Upon deploying the rotor 7 (after withdrawal of the cover hose 5 and expansion of the tube 1), the helix wire 8 contracts axially and takes the helical shape. In doing so, the band 9 also contracts and the cover 10 forms a smooth surface.

Although a preferred embodiment of the invention has been specifically illustrated and described herein, it is to be understood that minor variations may be made in the apparatus without departing from the spirit and scope of the invention, as defined the appended claims.

What is claimed is:

1. An axial-flow pump to be introduced intravascularly for cardiac support comprising a catheter and a drive shaft, a self-deploying and radially compressible flexible tube in combination with a self-deploying and radially compressible rotor within the tube, the tube being connected with the catheter and the rotor being connected with the drive shaft, extending coaxially in the catheter, the flexible tube is a self-deploying and radially compressible flexible tube dimensioned such that it can pass the aortal valve of the heart when deployed, the self-deploying rotor is a wire helix elongated when compressed and helical when deployed, both ends of which terminate in a central axis under an acute angle by an elastic band connecting both ends by extending along the central axis, and the rotor further including an elastic cover between the wire helix and the band.

2. The axial-flow pump of claim 1 wherein the self-deploying tube includes metal endoprosthetic material coated with plastic material.

3. The axial-flow pump of claim 1 wherein one end of the tube tapers in the manner of a funnel and is connected with the catheter.

4. The axial-flow pump of claim 2 wherein one end of the tube tapers in the manner of a funnel and is connected with the catheter.

5. The axial-flow pump of claim 1 wherein the tube has one of slit-shaped and circular openings in both end portions.

6. The axial-flow pump of claim 1 wherein the helix of the self-deploying rotor has at least one winding extending over 360°.

7. The axial-flow pump of claim 1 wherein the helix of the self-deploying rotor is made of memory metal.

8. The axial-flow pump of claim 6 wherein the helix of the self-deploying rotor is made of memory metal.

9. The axial-flow pump of claim 1 wherein the outer diameter of the self-deploying rotor is slightly smaller than the inner diameter of the deployed tube so that the rotor fills almost the entire cross section of the tube and is guided rotating in the tube.

10. The axial-flow pump of claim 1 wherein the rotor is centrally supported at one or both ends within the tube.

11. An axial-flow pump to be introduced intravascularly for cardiac support comprising a catheter and a drive shaft, a self-deploying and radially compressible flexible tube in combination with a self-deploying and radially compressible rotor within the tube, the tube being connected with the catheter and the rotor being connected with the drive shaft, extending coaxially in the catheter, the flexible tube is a self-deploying and radially compressible flexible tube dimensioned such that it can pass the aortal valve of the heart when deployed, an elastic helix connected with the drive shaft, a cover that unfolds when the helix is deployed.

12. The axial-flow pump of claim 11 wherein the self-deploying tube includes metal endoprosthetic material coated with plastic material.

13. The axial-flow pump of claim 11 wherein one end of the tube tapers in the manner of a funnel and is connected with the catheter.

14. The axial-flow pump of claim 11 wherein the tube has one of slit-shaped and circular openings in both end portions.

15. The axial-flow pump of claim 11 wherein the helix of the self-deploying rotor has at least one winding extending over 360°.

16. The axial-flow pump of claim 11 wherein the helix of the self-deploying rotor is made of memory metal.

17. The axial-flow pump of claim 11 wherein the outer diameter of the self-deploying rotor is slightly smaller than the inner diameter of the deployed tube so that the rotor fills almost the entire cross section of the tube and is guided rotating in the tube.

18. The axial-flow pump of claim 11 wherein the rotor is centrally supported at one or both ends within the tube.

* * * * *